United States Patent
Heanue et al.

(10) Patent No.: US 10,722,158 B2
(45) Date of Patent: Jul. 28, 2020

(54) HANDHELD OXIMETER PROBE WITH REPLACEABLE PROBE TIP

(71) Applicant: ViOptix, Inc., Newark, CA (US)

(72) Inventors: Joseph Heanue, Oakland, CA (US); Scott Coleridge, Belle Mead, NJ (US); Sophia Elizabeth Berger, Palo Alto, CA (US)

(73) Assignee: ViOptix, Inc., Newark, CA (US)

( * ) Notice: Subject to any disclaimer, the term of this patent is extended or adjusted under 35 U.S.C. 154(b) by 378 days.

(21) Appl. No.: 15/493,132

(22) Filed: Apr. 20, 2017

(65) Prior Publication Data

US 2018/0092581 A1 Apr. 5, 2018

Related U.S. Application Data

(60) Provisional application No. 62/363,562, filed on Jul. 18, 2016, provisional application No. 62/326,673, filed on Apr. 22, 2016, provisional application No. 62/326,644, filed on Apr. 22, 2016, provisional application No. 62/326,630, filed on Apr. 22, 2016, provisional application No. 62/325,413, filed on Apr.
(Continued)

(51) Int. Cl.
*A61B 5/1455* (2006.01)
*A61B 5/1495* (2006.01)
*A61B 5/00* (2006.01)

(52) U.S. Cl.
CPC ........ *A61B 5/14552* (2013.01); *A61B 5/1495* (2013.01); *A61B 5/14551* (2013.01); *A61B 5/0075* (2013.01); *A61B 5/742* (2013.01); *A61B 2560/0431* (2013.01); *A61B 2560/0443* (2013.01); *A61B 2560/0475* (2013.01)

(58) Field of Classification Search
CPC . A61B 5/0205; A61B 5/1455; A61B 5/14551; A61B 5/14552; A61B 5/742; A61B 5/1495; A61B 5/0075; A61B 2560/0443; A61B 2560/0475; A61B 2560/0431
See application file for complete search history.

(56) References Cited

U.S. PATENT DOCUMENTS 5,871,452 A * 2/1999 Baker .................... A61B 5/411
                                                      600/556
6,006,120 A * 12/1999 Levin .................. A61B 5/14552
                                                      600/323
(Continued)

FOREIGN PATENT DOCUMENTS

EP        0102816 A2    3/1984
EP        1889569 B1    6/2014
(Continued)

OTHER PUBLICATIONS

International Search Report, PCT Application PCT/US2017/028701, dated Oct. 24, 2017, 6 pages.

*Primary Examiner* — Eric F Winakur
*Assistant Examiner* — Chu Chuan Liu
(74) *Attorney, Agent, or Firm* — Aka Chan LLP

(57) ABSTRACT

A handheld oximeter probe has a replaceable probe tip. The probe tip can be removed or detached from the probe unit and discarded. A replacement probe tip can be attached to the probe tip. The replaceable probe tip allows the probe unit to be reused many times, each time with new sterile probe tip.

23 Claims, 10 Drawing Sheets

Related U.S. Application Data 20, 2016, provisional application No. 62/325,416, filed on Apr. 20, 2016, provisional application No. 62/325,403, filed on Apr. 20, 2016.

(56) References Cited

U.S. PATENT DOCUMENTS

| | | | |
|---|---|---|---|
| 6,095,974 A * | 8/2000 | Shemwell | A61B 5/14552 600/310 |
| 6,385,821 B1 | 5/2002 | Modgil et al. | |
| 7,236,813 B2 | 6/2007 | Parker | |
| 8,233,955 B2 | 7/2012 | Al-ali et al. | |
| 8,938,279 B1 | 1/2015 | Heaton, II et al. | |
| 2003/0009092 A1 | 1/2003 | Parker | |
| 2004/0034294 A1 | 2/2004 | Kimball et al. | |
| 2006/0053522 A1 | 3/2006 | Kimbell | |
| 2007/0244377 A1 | 10/2007 | Cozad et al. | |
| 2008/0319290 A1 | 12/2008 | Mao et al. | |
| 2009/0253968 A1 | 10/2009 | Cho et al. | |
| 2010/0005630 A1 | 1/2010 | Gitman et al. | |
| 2010/0292549 A1 | 11/2010 | Shuler | |
| 2010/0298728 A1 | 11/2010 | Addison et al. | |
| 2011/0205535 A1 | 8/2011 | Soller et al. | |
| 2011/0224518 A1 | 9/2011 | Tindi et al. | |
| 2011/0276276 A1 | 11/2011 | Kashyap et al. | |
| 2012/0289801 A1 | 11/2012 | Yamaguchi | |
| 2013/0023743 A1 | 1/2013 | Al-ali et al. | |
| 2013/0317331 A1 | 11/2013 | Bechtel et al. | |
| 2014/0046152 A1 | 2/2014 | Bechtel et al. | |
| 2014/0180043 A1 | 6/2014 | Addison et al. | |
| 2014/0288386 A1 | 9/2014 | Zand et al. | |

FOREIGN PATENT DOCUMENTS

| | | |
|---|---|---|
| WO | 2009090665 A1 | 7/2009 |
| WO | 2010011763 | 1/2010 |
| WO | 2010042264 A1 | 4/2010 |
| WO | 2014026200 | 2/2014 |

\* cited by examiner

HANDHELD OXIMETER PROBE WITH REPLACEABLE PROBE TIP

CROSS-REFERENCE TO RELATED APPLICATIONS

This application claims the benefit of the following U.S. patent applications 62/325,403, 62/325,416, and 62/325,413, filed Apr. 20, 2016, 62/326,630, 62/326,644, and 62/326,673, filed Apr. 22, 2016, and 62/363,562, filed Jul. 18, 2016. These applications are incorporated by reference along with all other references cited in these applications.

BACKGROUND OF THE INVENTION

The present invention relates to compact, handheld tissue oximeters, that include sources and detectors located on detachable, replaceable probe tips.

Oximeters are medical devices used to measure oxygen saturation of tissue in humans and living things for various purposes. For example, oximeters are used for medical and diagnostic purposes in hospitals and other medical facilities (e.g., operating rooms for surgery, recovery room for patient monitoring, or ambulance or other mobile monitoring for, e.g., hypoxia); sports and athletic purposes at a sports arena (e.g., professional athlete monitoring); personal or at-home monitoring of individuals (e.g., general health monitoring, or person training for, such as a marathon); and veterinary purposes (e.g., animal monitoring).

In particular, accessing a patient's oxygen saturation, at both the regional and local level, is important as it is an indicator of the state of the patient's health. Thus, oximeters are often used in clinical settings, such as during surgery and recovery, where it can be suspected that the patient's tissue oxygenation state is unstable. For example, during surgery, oximeters should be able to quickly deliver accurate oxygen saturation measurements under a variety of non-ideal conditions. While existing oximeters have been sufficient for post-operative tissue monitoring where absolute accuracy is not critical and trending data alone is sufficient, accuracy is, however, required during surgery in which spot-checking can be used to determine whether tissue can remain viable or needs to be removed.

Pulse oximeters and tissue oximeters are two types of oximeters that operate on different principles. A pulse oximeter requires a pulse in order to function. A pulse oximeter typically measures the absorbance of light due to pulsing arterial blood. In contrast, a tissue oximeter does not require a pulse in order to function, and can be used to make oxygen saturation measurements of a tissue flap that has been disconnected from a blood supply.

Human tissue, as an example, includes a variety of light-absorbing molecules. Such chromophores include oxygenated and deoxygenated hemoglobins, melanin, water, lipid, and cytochrome. Oxygenated and deoxygenated hemoglobins are the most dominant chromophores in tissue for much of the visible and near-infrared spectral range. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, reducing cost of use and reuse. Therefore, there is a need for an improved tissue oximetry devices and methods of making measurements using these devices.

BRIEF SUMMARY OF THE INVENTION

A wireless, handheld tissue oximeter is provided that has a probe unit and a detachable, replaceable probe tip that is detachable from the probe unit. The probe unit and probe tip operate as a tissue oximeter when coupled.

The probe tip contacts patient tissue when used and can potentially be contaminated with patient tissue or fluid while the probe unit does not come in contact with the patient. The probe tip and any contamination on the probe tip can be removed from the probe unit and replaced with a different probe tip, such as a new clean probe tip or a new sterile probe tip. Removal of the potentially contaminated probe tip allows for the probe unit's reuse.

The more expensive electronic, optical components or both can be located in the probe unit allowing for reuse of these expensive components and therefore providing a cost savings with the reuse. Specifically, the probe unit can include self-contained optics (sources and detectors), computer processing, a display, and a power-supply (battery). The oximeter can be used in a surgical, sterile environment for spot measurements, or clean environments that are not necessarily sterile.

In an implementation, a tissue-oximeter system includes a tissue-oximeter probe unit comprising: a handheld housing; a processor housed in the handheld housing; a memory, housed in the handheld housing, electronically coupled to the processor; a display, accessible from an exterior of the handheld housing, electronically coupled to the processor; and a battery, housed in the handheld housing, coupled to and supplies power to the processor, the memory, and the display. The handheld housing includes a first connector having a lip distally positioned from the display.

The tissue-oximeter system includes a first probe tip comprising a first plurality of source structures having a first source structure arrangement; a first plurality of detector structures having a first detector structure arrangement; and a second connector having a top edge. The lip of the first connector abuts the top edge of the second connector when the first probe tip is removably coupled to the handheld housing.

In an implementation, a method includes providing a handheld oximeter housing; providing a processor housed in the handheld oximeter housing; providing a memory, housed in the handheld oximeter housing, electronically coupled to the processor; providing a display, accessible from an exterior of the handheld oximeter housing, electronically coupled to the processor; providing a battery, housed in the handheld oximeter housing; and allowing for the battery to supply power to the processor, the memory, and the display. A first connector is proved on the handheld oximeter housing having a lip that is distally positioned from the display on the handheld oximeter housing.

The method includes providing a first probe tip; providing a first plurality of source structures on a face of the first probe tip, wherein the first plurality of source structures has a first source structure arrangement; and providing a first plurality of detector structures on the face of the first probe tip. The first plurality of detector structures has a first detector structure arrangement. A second connector is provided on a top edge of the first probe tip.

The method includes allowing for removably coupling the first probe tip to the handheld oximeter housing via coupling the first connector to the second connector; and allowing for the lip of the first connector to abut the top edge of the second connector.

In an implementation, a method includes providing a handheld oximeter housing; providing a processor housed in the handheld oximeter housing; providing a memory, housed in the handheld oximeter housing, electronically coupled to the processor; providing a display, accessible from an exterior of the handheld oximeter housing, electronically coupled to the processor; providing a battery, housed in the handheld oximeter housing; and allowing for the battery to supply power to the processor, the memory, and the display. A first connector is provided having a lip that is distally positioned from the display on the handheld oximeter housing. A first probe tip is provided that includes a second connector having a first top edge.

The method includes coupling the first probe tip to the handheld oximeter housing via coupling the first connector to the second connector and contacting the lip of the first connector to abut the first top edge of the second connector.

A second probe tip is provides that has a third connector with a second top edge. The method includes replacing the first probe tip with the second probe tip by coupling the second probe tip to the handheld oximeter housing by coupling the first connector to the third connector and contacting the lip of the first connector to abut the second top edge of the third connector. As such, the probe unit is reusable with the second probe tip attached thereby saving costs with the reuse. The first probe tip can be also be reused after being cleaned, sterilized, or both.

Other objects, features, and advantages of the present invention will become apparent upon consideration of the following detailed description and the accompanying drawings, in which like reference designations represent like features throughout the figures.

DETAILED DESCRIPTION OF THE INVENTION

The present invention generally relates to a wireless, handheld oximeter prove for measuring local (regional) tissue oxygen. The oximeter probe has a probe unit and probe tip that is detachable from the probe unit.

Figure 1A:
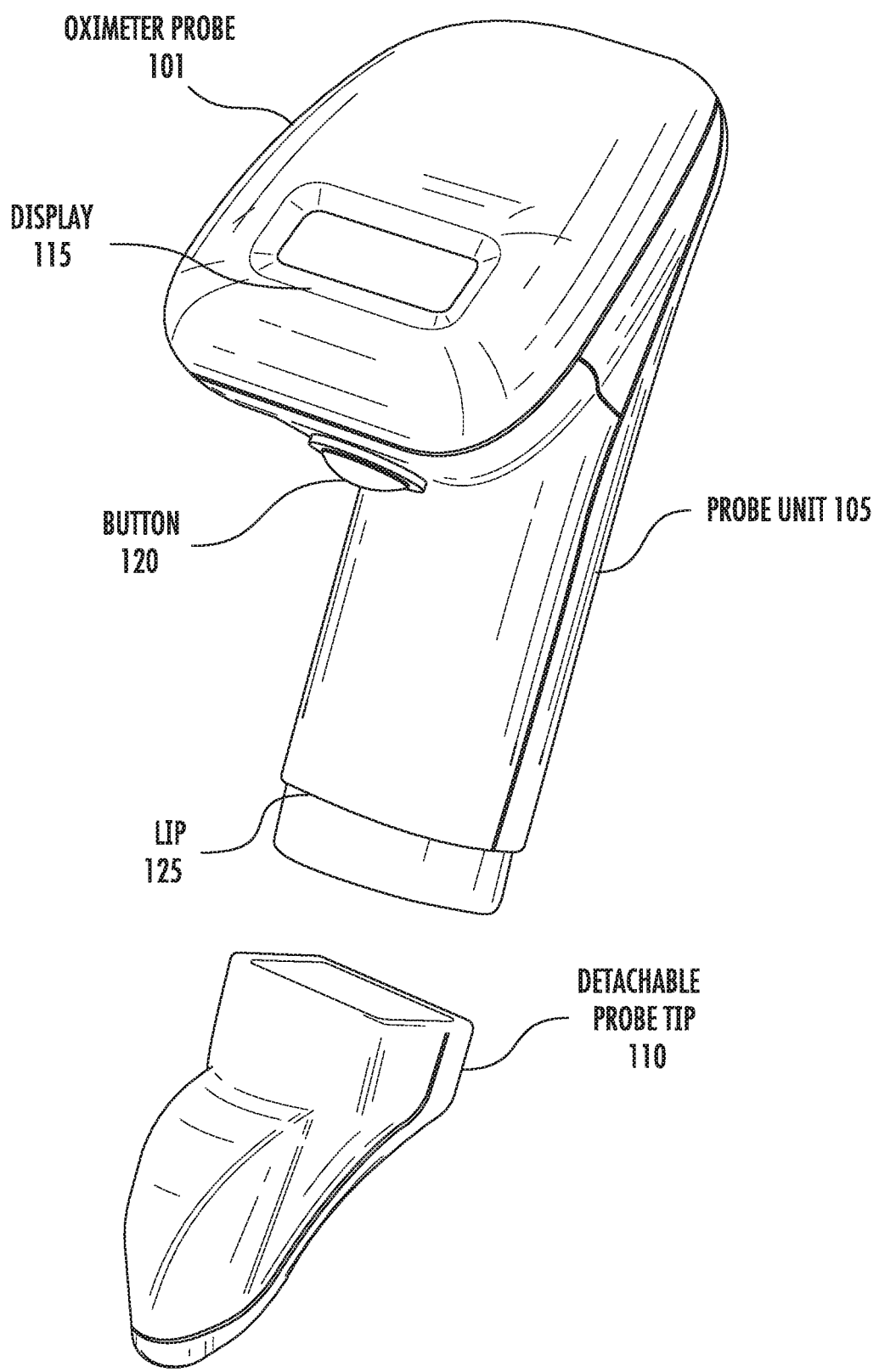
FIG. 1A shows a diagram of an oximeter prove having a probe unit and a detachable probe tip.

FIG. 1A shows a handheld oximeter probe 101. This oximeter probe is used to make oxygen saturation measurement of target tissue. In an implementation, the oximeter probe is a tissue oximeter, but in other implementation, the oximeter probe can be a pulse oximeter.

Oximeter probe 101 has two portions, a probe unit 105 and probe tip 110, which can be detached from the probe unit and replaced with another replacement probe tip. When the probe unit 105 and probe tip 110 are attached together, the oximeter probe operates as a standalone handheld oximeter, without the need to be attached by cabling to another unit.

The oximeter probe has a display 115 (e.g., an LCD display) and a button 120. When the button is depressed, light is emitted at the probe tip into a target tissue to be measured, and reflected light from the target tissue is received at the probe tip. From the received light, the probe determines a measured oxygen saturation for the tissue. An indicator (e.g., a numerical value) for the measured oxygen saturation is displayed on the display.

The oximeter probe is shaped ergonomically to comfortably fit in a user's hand. During use, the probe is held in a user's hand between a user's thumb and fingers. The display faces generally upward (e.g., away from the tissue being measured) within view of the user's eyes when a face of the probe (not shown) is directed away from the user and faces toward the target tissue to be measured.

The following patent applications describe various oximeter devices and oximetry operation, and discussion in the following applications can be combined with aspects of the invention described in this application, in any combination. The following patent application are incorporated by reference along with all references cited in these application Ser. No. 14/944,139, filed Nov. 17, 2015, Ser. No. 13/887,130 filed May 3, 2013, Ser. No. 15/163,565, filed May 24, 2016, Ser. No. 13/887,220, filed May 3, 2013, Ser. No. 15/214,355, filed Jul. 19, 2016, Ser. No. 13/887,213, filed May 3, 2013, Ser. No. 14/977,578, filed Dec. 21, 2015, Ser. No. 13/887,178, filed Jun. 7, 2013, Ser. No. 15/220,354, filed Jul. 26, 2016, Ser. No. 13/965,156, filed Aug. 12, 2013, Ser. No. 15/359,570, filed Nov. 22, 2016, Ser. No. 13/887,152, filed May 3, 2013, Ser. No. 29/561,749, filed Apr. 16, 2016, 61/642,389, 61/642,393, 61/642,395, 61/642,399 filed May 3, 2012, and 61/682,146, filed Aug. 10, 2012.

In an implementation, the probe tip slides onto the probe unit and can lock or snap into place on the probe unit. The probe tip has an opening that receives a corresponding fitting of the probe unit for connecting the probe tip to the probe unit. The probe tip opening has a first diameter or dimension that will fit over the corresponding fitting of the probe unit. The fitting of the probe unit has a second diameter or dimension that is less than the first diameter or dimension.

A user slides the probe unit onto the fitting of the probe unit until the probe tip is pushed against a ridge or lip 125 of the fitting, which serves as a stop mechanism. The fitting can have one or more O-rings or other sealing mechanisms to help maintain a proper seal between the opening of the probe unit and the fitting of the probe tip to prevent tissue and fluid from getting inside the assembled oximeter probe. When assembled, an outer surface of the probe tip will be flush with an outer surface of the probe unit.

This specific implementation has a specific attachment mechanism where the probe tip slides onto the probe unit. However, as can be appreciated, many other attachment mechanisms can be used instead or in combination. For example, the probe unit can have an opening that slides onto a corresponding fitting of the probe tip. The attachment mechanism can use a twist-on (e.g., twist-lock mechanism) or screw-on mechanism. The attachment mechanism can include a latch. For example, when the probe tip is slid onto the probe unit, the latch locks the probe tip into place. Then the latch can be depressed or otherwise unlatched, which allows the probe tip to be separated from the probe unit. The attachment mechanism can have a shape (e.g., oval, elliptical, triangular, or other arbitrary shape) that allows the probe tip and probe unit to be attached in one particular orientation. The attachment mechanism can include a keying mechanism, such as one or more notches at specific locations of the fitting, that allow the probe tip and probe unit to be attached in a particular orientation. The attachment mechanism can include one or more connectors that securely hold the first and second housing together after the probe unit and probe tip are mated, such as detents, screws, one or more magnets, and other mechanisms.

Figure 1B:
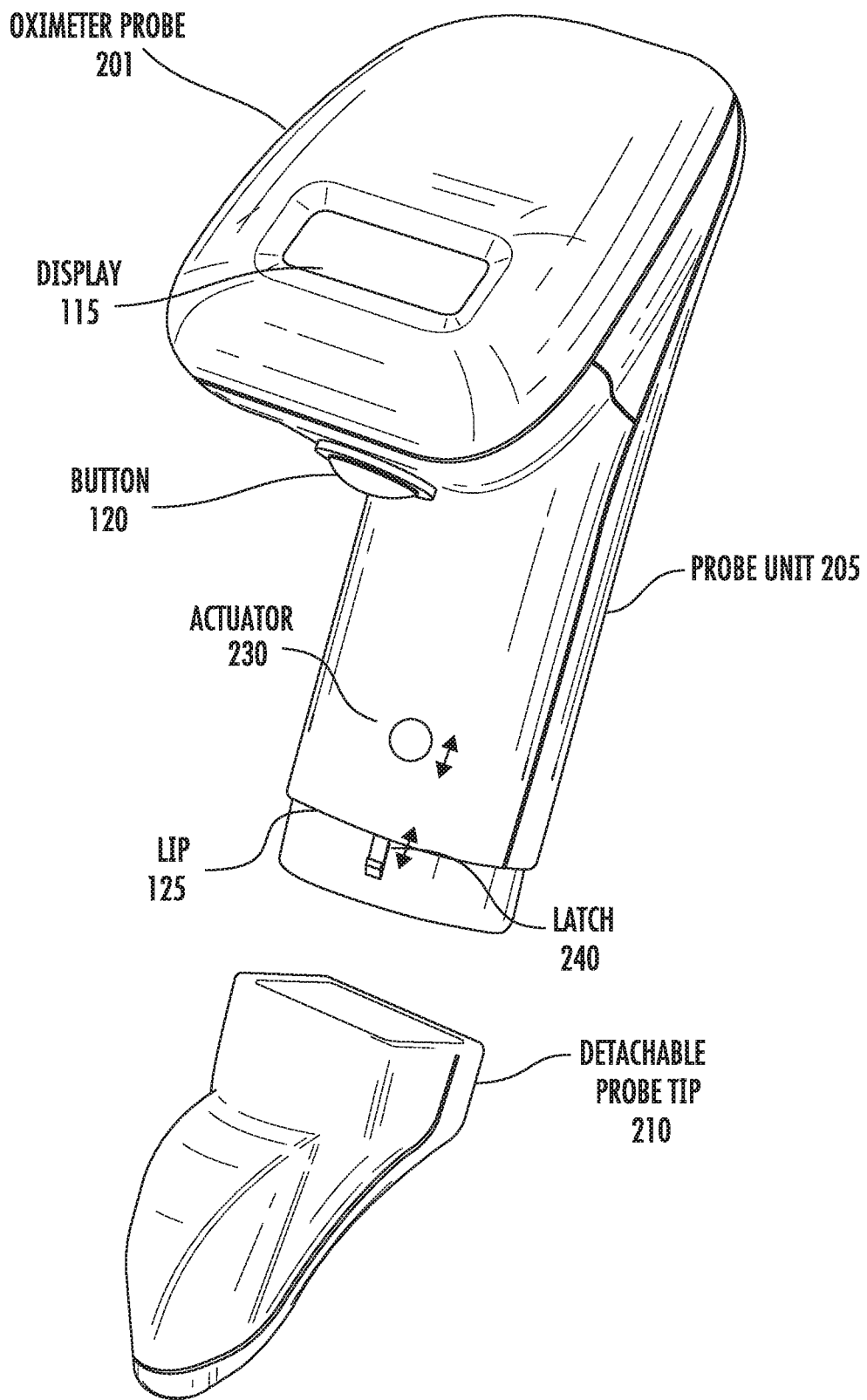
FIG. 1B shows a diagram of an oximeter prove having a probe unit and a detachable probe tip.

FIG. 1B shows a handheld oximeter probe 201. This oximeter probe has a probe tip 210 that is detachable from the probe unit 205. The detachable probe tip can be replaced with the same probe tip or a different probe tip. The probe unit includes an actuator 230 and a latch 240 that is activated by the actuator. The latch latches to a receptacle on the probe tip when the probe unit and probe tip are connected. When the latch is coupled to the receptacle, the connection holds the probe tip on the probe unit and inhibits the probe tip from disconnecting from the probe unit. Activation of the actuator sufficiently decouples the latch from the receptacle allowing from relatively easy removal of the probe tip from the probe unit.

The actuators can include one or more of a variety of devices, such as a button, a slider, a knob, a switch, or other device. The latch can include one or more of a variety of devices, such as a slider, a hook, a magnet, a detent element, a hook, or other device. The latch can be spring loaded by a spring mechanism. The spring mechanism places a spring force on the latch to couple to the latch to the receptacle. The actuator when activated overcomes the spring force of the latch decoupling the latch from the receptacle. The receptacle can be one more of a detent element, an aperture, a hook, a magnet, or other device that couples to the latch.

In an implementation, the actuator and latch form a portion of the probe tip, and the receptacle forms a portion of the probe unit. In another implementation, the actuator is coupled to the receptacle for decoupling the receptacle from the latch. In another implementation, the latch is accessible from the surface of the probe unit or probe tip and is adapted to be pressed by a user to release the latch from the receptacle.

The button can be activated by a user by one or more of a variety of actions, such as being depressed, slid, or other manipulations. When the button is activated, the latch device uncouples from the receptacle and allows for the probe tip to be detached from the probe unit. For example, when the button is activated, the latch can be moved away from the receptacle unlatching the probe tip from the probe unit.

In an implementation, the probe unit includes two or more actuators and two or more latches, and the probe tip includes two or more receptacles. Alternatively, the probe tip includes the two or more actuators and the two or more latches, and the probe unit includes the two or more receptacles. The actuators and latches can be positioned on opposite sides of the probe unit or probe tip, which allows the actuators to be simultaneously actuated (e.g., buttons pressed), for example, by pressing on the actuators with opposing fingers.

Figure 1C:
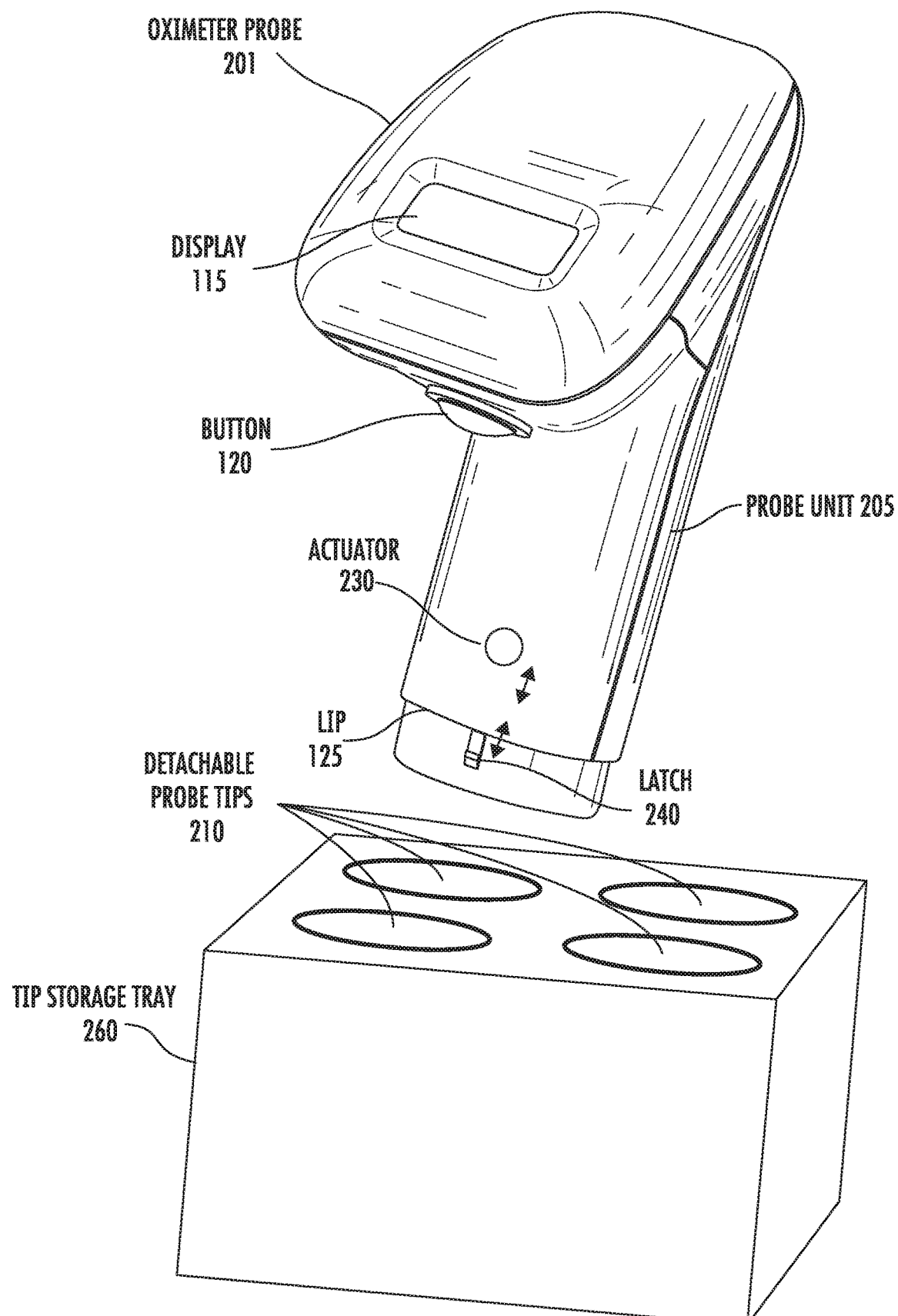
FIG. 1C shows a tip storage tray that includes a number of openings that are adapted for storing a corresponding number of probe tips.

FIG. 1C shows a tip tray 260 that includes a number of openings that are adapted for storing a number of probe tips 210. The tip tray provides protection to the probe tips during transport, storage, use, and after usage.

The tip tray facilitates coupling and decoupling the probe tips to the probe unit. Specifically, a probe tip can be removed from the tip tray by inserting the end of the probe unit into the base opening of the probe tip where the latch latches to the probe tip. Thereafter, the probe tip can be lifted from the tip tray by the probe unit.

After use, the probe tip can be discarded or returned to one of the openings in the tip tray and the actuator actuated to release the latch from the probe tip, which facilitates release of the probe tip from the probe unit. Thereafter, the same or a different probe tip can be attached to the probe unit by repeating the above steps. While probe tray 260 is shown as including four openings housing four probe tips, the probe tray can include more or fewer openings for housing more or fewer probe tips. In this implementation, the probe tips are cartridge devices where the cartridges can easily be attached and detached from the probe unit.

The probe tips can be maintained in a hygienic or sterile environment in the probe tray prior to use of the probe tips. After use, the used probe tip can be discarded and a different probe tip that is sterile can be retrieved from the probe tray and attached to the probe unit.

In an implementation, a tissue oximeter that includes a base unit and cable connected probe is adapted for use with detachable probe tips. The detachable probe tips can be coupled to and decoupled from the cable connected probe as described above. Such coupling and decoupling allows for not only the base unit to be repeatedly used with a number of patients, the cable connected probe can similarly be used with a number of patients where the probe tip may be changed for use with each patient.

The probe tip can be detached from the probe unit and replaced by the user with another probe tip. This allows the probe unit to be reused with multiple disposable probe tips. For example, after using a sterile or clean first probe tip with a first patient, the user can detach the first probe tip and dispose of or clean the first probe tip. Then the user can attach a sterile or clean second probe tip to use for a second patient. By having replaceable probe tips, this allows for probe unit to be used multiple times without being disposed of, which reduces cost of use. Further, the more expensive elements (e.g., electronic components) of the oximeter probe can be located in the reusable probe unit and the less expensive elements can be located in the probe tip further reducing the cost of use.

Further, different types of probe tips can be supplied for specific uses or purposes. For example, there may be specific probe tips with different orientations, different numbers or types of sensors and detectors for different tissue types or measuring different locations (e.g., external and external uses) in the body. In an implementation, a first probe tip used with the probe unit can have a first configuration of sources and detectors and a second probe tip used with the probe unit can have a second configuration where the first and second configurations are different configuration. The different configurations of sources and detectors can include different distances between at least one source and one detector of the first and second configurations. The different source to detector configurations can be used for probing different tissue depths (e.g., depth from tissue surface into the tissue) of tissue. For example, relatively large source to detector separations of a first probe tip can be used for probing relatively deep tissue depths, and shorter to detector spacing can be used to probe shallower tissue depths. In some implentations, different source wavelengths are used with the different configurations of sources and detector to facilitate probing the different tissue depths, such as using relatively long wavelength (e.g., IR) for deeper tissue depth probing and shorter wavelengths (e.g., visible and IR or shorter wavelength IR) for shallower tissue depth probing. The source to detector separations can vary from about 0.5 millimeters to about 10 millimeters.

Figure 1D:
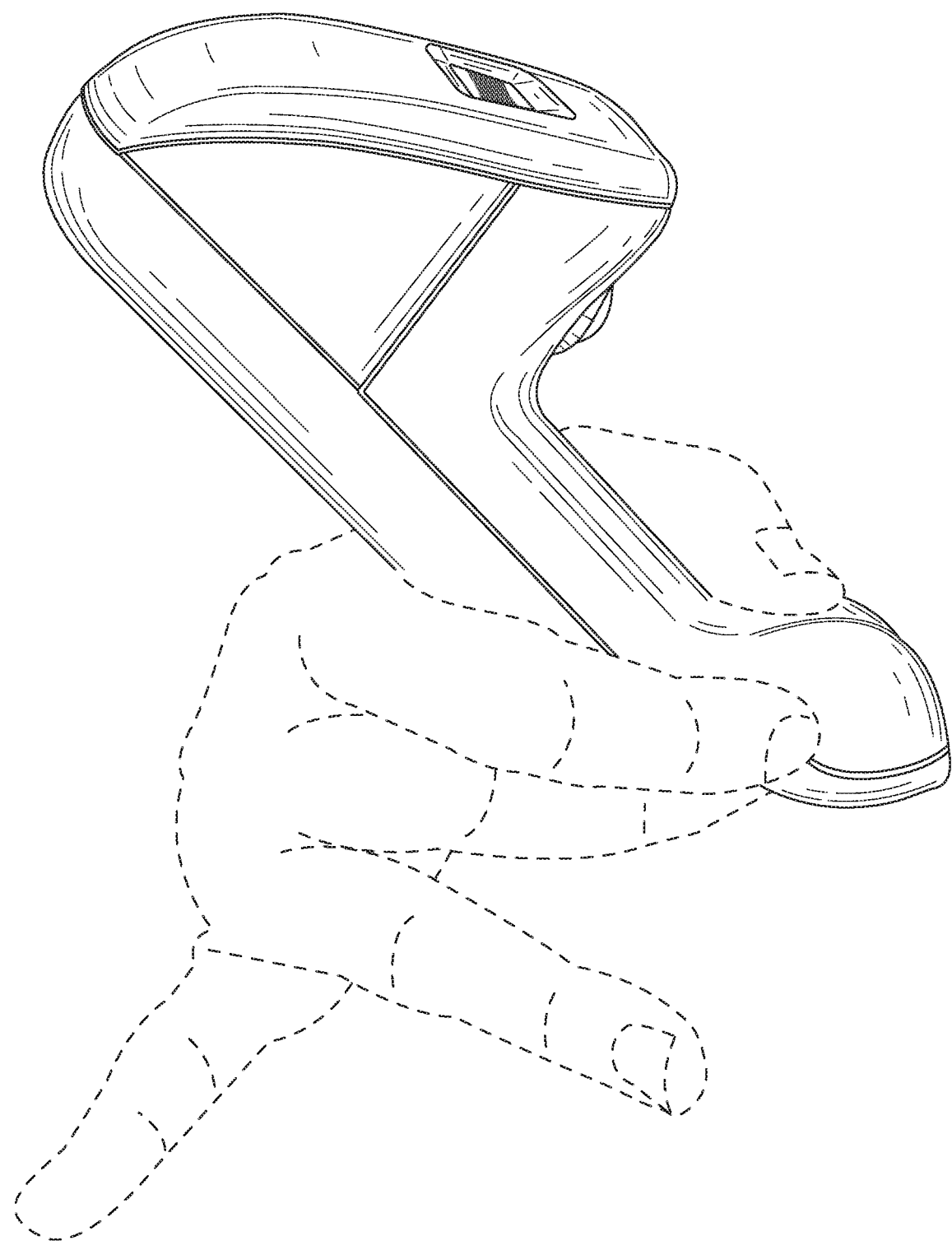
FIG. 1D show the probe tip coupled to the probe unit and shows the oximeter probe in use.

FIG. 1D show the probe tip coupled to the probe unit and shows the oximeter probe in use, being gripped by a hand of a user. FIG. 1D shows the grip locations for the thumb and middle finger on the probe tip so the fingers and hand do not obstruct the view of the display and the tissue being probed by the probe. The index finger is against a side of the device (e.g., probe tip), while the ring finger and pinky are point away from the sensor head, toward the back of the device. The probe unit (e.g., probe unit housing) and the probe tip (e.g., probe tip housing) held together form the operating oximeter probe. A hand of a user holds the oximeter probe, such that the thumb and index finger of the user will grip the probe tip (e.g., probe tip housing) while the probe unit (e.g., probe unit housing) is cradled by a webbing between the thumb and index finger of the same hand. In the oximeter probe formed by the probe unit and the probe tip, the display and probe face of the probe tip face away from each other. Further, with the hand holding the oximeter device, with the probe face on tissue to be measured the display is directed away from the tissue (e.g., up) and does is located back from the probe face, such that the probe tip and tissue that is being measured is not blocked (e.g., visually obstructed) by the probe unit and display. The display directed away from the probe face is viewable by a user during use of the oximeter probe.

Figure 2:
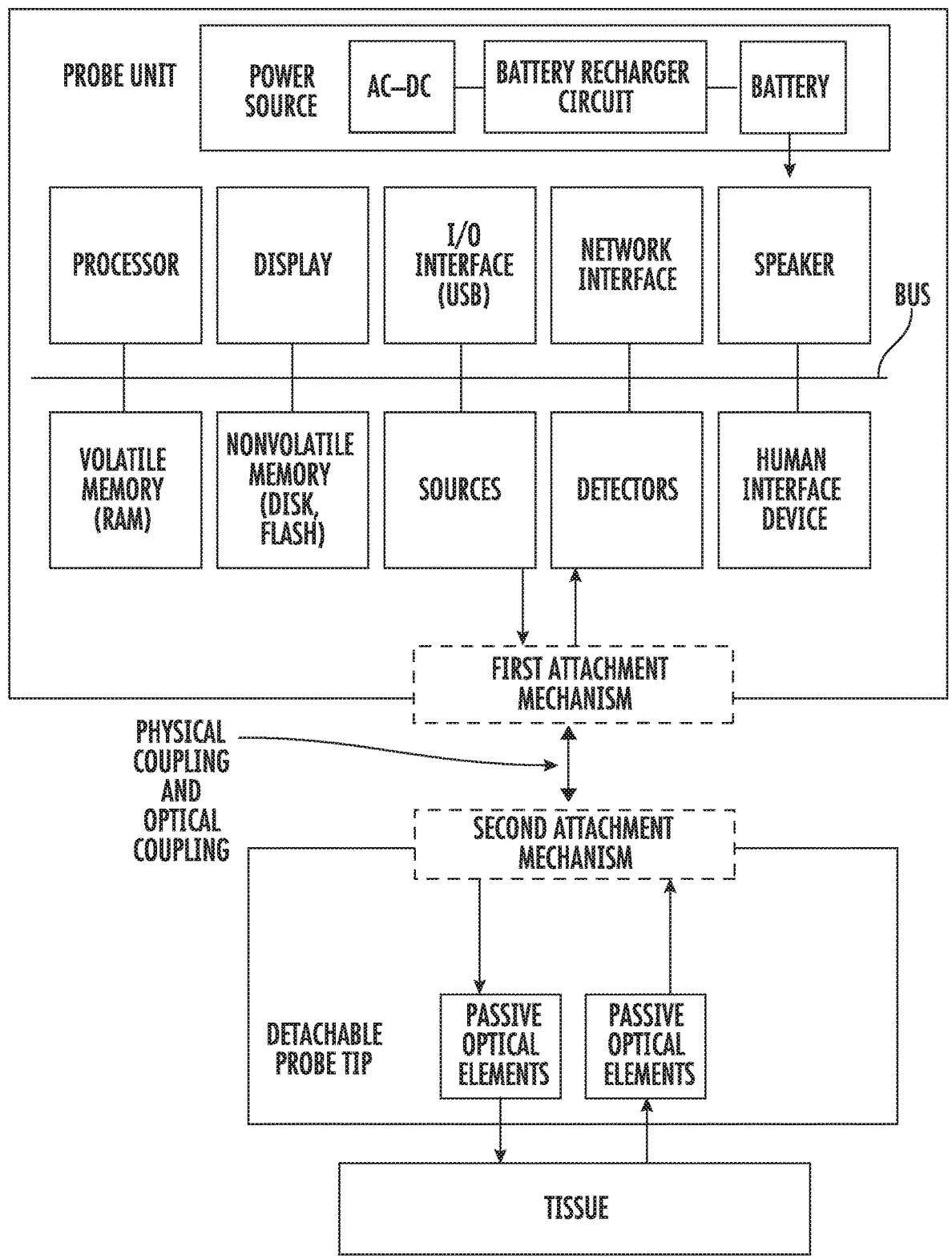
FIG. 2 shows a block diagram of an oximeter probe that has a number of electronic components, such as the sources and detectors, located in the probe unit and passive optical devices located in the probe tip.

FIG. 2 shows a block diagram of an oximeter probe that has a number of electronic components, such as the sources and detectors, located in the probe unit and passive optical devices located in the probe tip. The attachment mechanisms of the probe unit and probe tip physically connect and disconnect as described and provide optical coupling between the probe unit and probe tip for transferring radiation signal between the probe unit and probe tip. The probe unit can include a number of other electronic components, such as a processor, memories, and other components.

The sources in the probe unit can be LEDs, OLEDs, quantum dot LEDs, laser diodes, or other diode types. The detectors can be photodetectors, such as photodiodes, photoresistors, phototransistors, quantum dot photodiodes, reverse biased LEDs, CMOS detectors, or other detector types.

Figure 3:
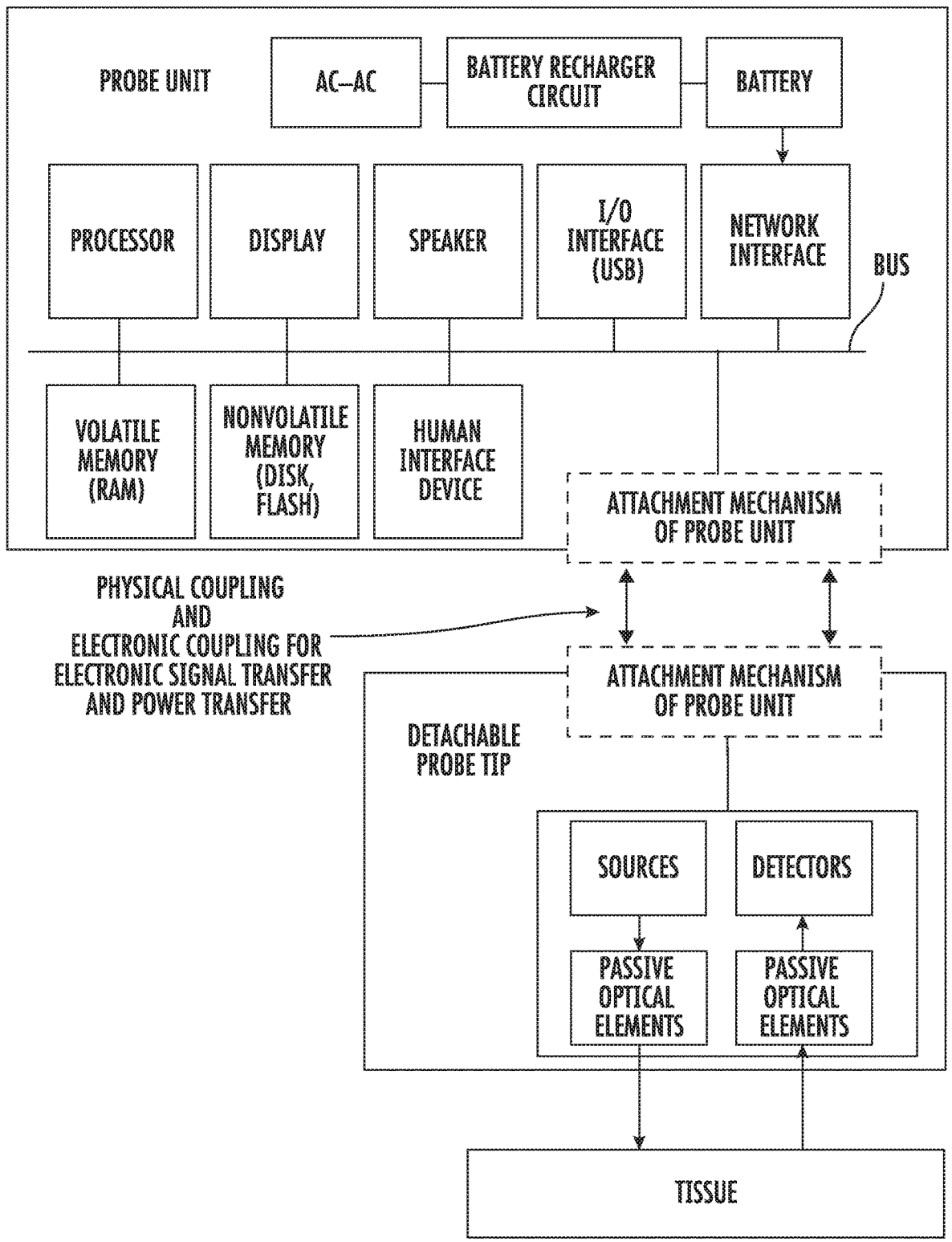
FIG. 3 shows a block diagram of an oximeter probe where the sources and detectors are located in the probe tip while other electronic components are located in the probe unit.

FIG. 3 shows a block diagram of an oximeter probe where the sources and detectors are located in the probe tip while other electronic components are located in the probe unit. In this implementation, the attachment mechanisms both include electrical connectors for transferring electrical signals from the electronic components (e.g., the processor) in the probe unit to the sources and for receiving electrical signals generated and transmitted by the detectors for reflected radiation received from the tissue.

The electrical connectors of the probe unit electrically couple with the electrical connectors of the detachable probe tip when the probe unit and the detachable probe tip are coupled, such as when the detachable probe tip is slid onto the probe unit and an edge of one of the detachable probe tip and probe unit contacts a lip of the other of the probe tip and probe unit. The electrical connectors decouple when the detachable probe tip is detached from the probe unit. When a different detachable probe tip is coupled to the probe unit, the electrical connectors of the different detachable probe tip electrically coupled with the electrical connectors of the probe unit.

The electrical connectors can also transfer power supplied from a battery that is located in the probe unit to the sources and detectors that are located in the probe tip to power the sources and detectors. The source and detectors can transmit and receive light (e.g., infrared light) via one or more passive optical elements, which might include a protective epoxy layer (e.g., a 100 micrometer to 150 micrometer epoxy layer) that is posited over the sources and detectors, one or more lenses, or other classical optics devices. An outer surface of the epoxy layer can be the face of the probe tip that contacts tissue to be probed by the oximeter.

Figure 4A:
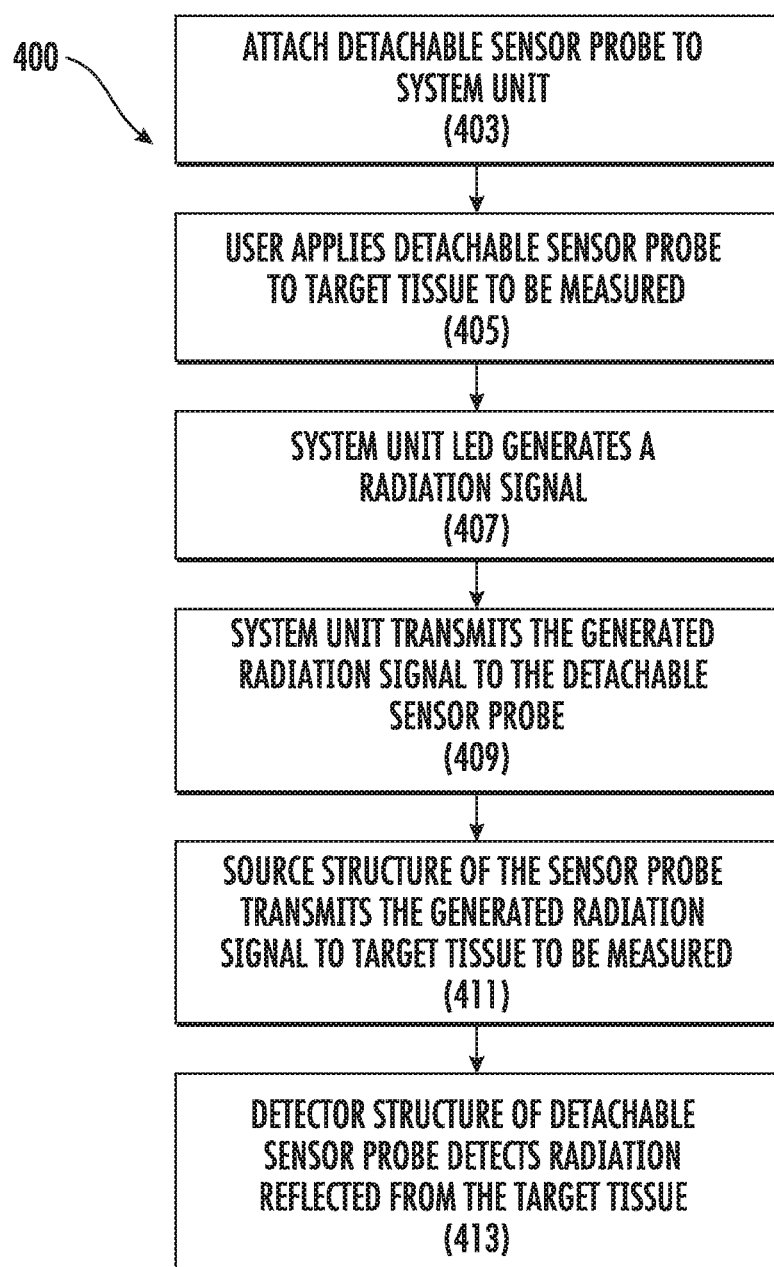
FIGS. 4A-4B show a flow diagram for the operation of an oximeter probe where optical signals are transferred between the probe unit and the probe tip.
Figure 4B:
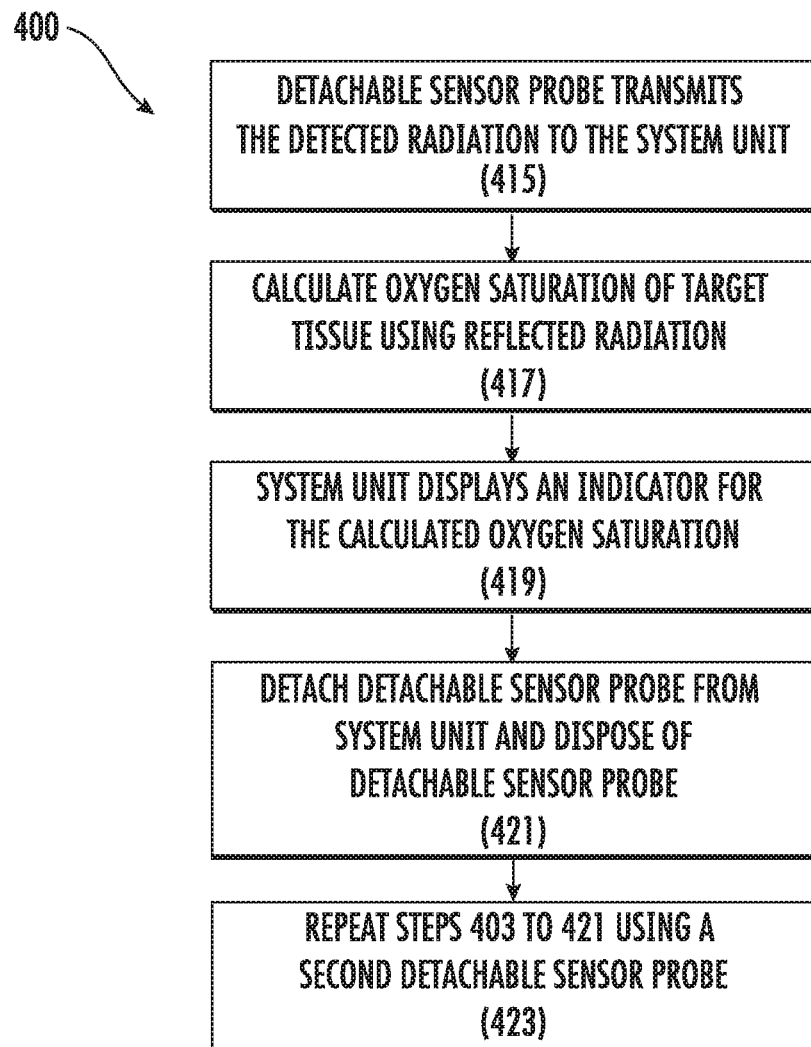

FIGS. 4A-4B show a flow diagram 400 for the operation of an oximeter probe where optical signals are transferred between the probe unit and the probe tip. Steps can be added to the flow diagram, removed from the flow diagram, or combined without deviating from the scope of the implementation.

At 403, a detachable sensor probe (e.g., probe tip) is attached to the system unit to form an operational oximeter probe. At 405, the sensor probe is contacted to target tissue for with a tissue reading is to be made, such as blood oxygen saturation measurement. At 407, the system unit LED generated radiation that is transmitted (at 409) into the detachable sensor probe.

At 411, the source structures (e.g., light transmission ports) in a probe face (e.g., an optical sensor) of the probe tip that are optically coupled, such as via waveguides (e.g., optical fibers to the sources, such as LEDs) of the sensor probe transmit the generated radiation signal into the target issue to be measured. At 413, the detector structures (e.g., light receiving ports on the probe face of the probe tip that are optically coupled to the photodetectors) of detachable sensor probe detect radiation reflected from the target tissue.

At 415, the detachable sensor probe transmits the detected radiation to the system unit, which calculates oxygen saturation of target tissue using the reflected radiation (at 417). At 419, the system unit displays an indicator for the calculated oxygen saturation on the display of the unit.

At 421, the detachable sensor probe is detached from system unit and can be disposed of or saved for later use. Thereafter, steps 403 to 421 can be repeated using second detachable sensor probe that is a difference sensor probe from the first sensor probe, or the first sensor probe, if saved, can be reattached to the probe unit for addition use.

Figure 5A:
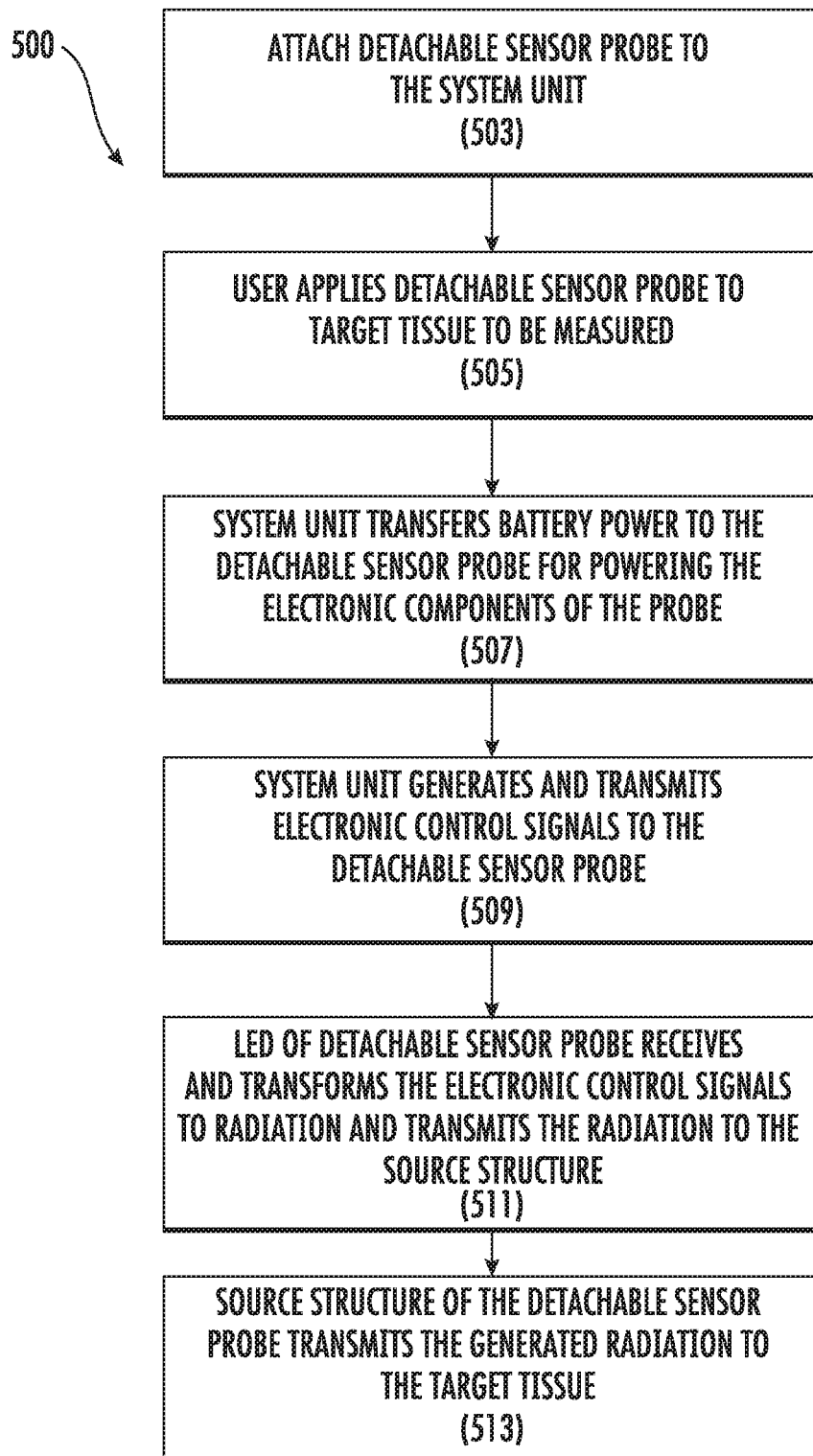
FIGS. 5A-5B show a flow diagram for the operation of an oximeter probe where electrical signals and power are transferred between the probe unit and the probe tip.
Figure 5B:
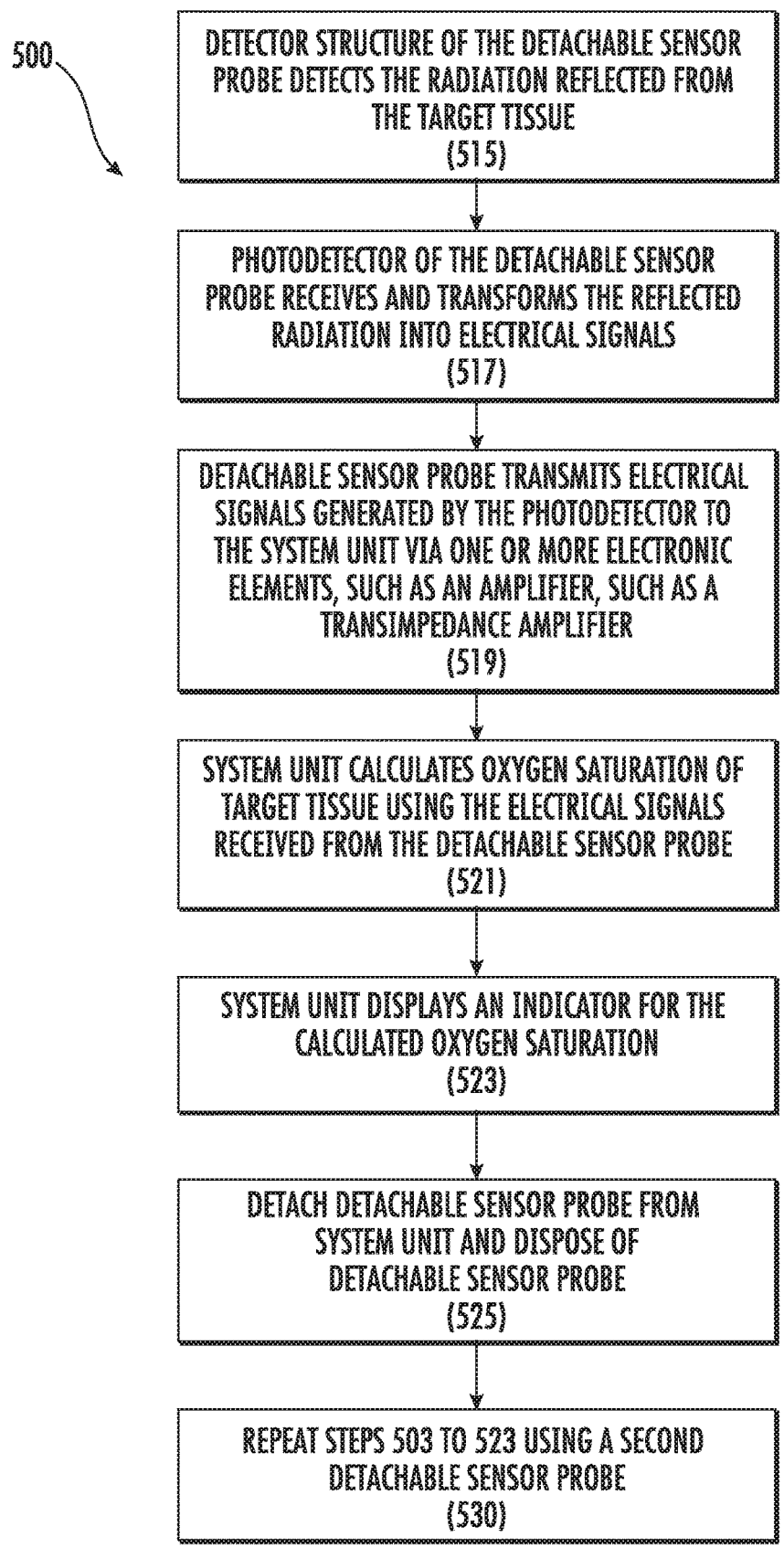

FIGS. 5A-5B show a flow diagram 500 for the operation of an oximeter probe where electrical signals and power are transferred between the probe unit and the probe tip. Steps can be added to the flow diagram, removed from the flow diagram, or combined without deviating from the scope of the implementation.

At 501, a detachable sensor probe is attached to the system unit. At 505, the sensor probe is contacted to target tissue for with a tissue reading is to be made, such as blood oxygen saturation measurement. At 507, the system unit transfers battery power to the detachable sensor probe for powering the electronic components (e.g., LEDs, photodetector, transimpedance amplifiers, or other components) of the probe. At 509, the system unit generates and transmits electronic control signals to the detachable sensor probe.

At 511, the LEDs of detachable sensor probe receive and transform the electronic control signals to radiation and transmit the radiation to the source structures of the probe tip. At 513, the source structures of the detachable sensor probe transmit the generated radiation to the target tissue.

At 515, the detector structures of the detachable sensor probe detect the radiation reflected from the target tissue. At 517, the photodetectors receives and transforms the reflected radiation into electrical signals. Thereafter at 519, the detachable sensor probe transmits electrical signals generated by the photodetector to the system unit via one or more electronic elements, such as the transimpedance amplifiers, which transform the current signals into voltage signals.

At 521, the system unit calculates an oxygen saturation value for the target tissue using the electrical signals received from the detachable sensor probe. At 523, the system unit displays an indicator for the calculated oxygen saturation value on the display of the system unit.

At 525, the detachable sensor probe is detached from the system unit and is dispose of or saved for later use. Thereafter, steps 503 to 423 can be repeated using second detachable sensor probe that is a difference sensor probe from the first sensor probe, or the first sensor probe, if saved, can be reattached to the probe unit for addition use.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. An oximeter device comprising:
a first housing portion comprising:
a processor housed in the first housing portion;
a display, accessible from an exterior of the first housing portion, electronically coupled to the processor; and
a first electrical connector electronically coupled to the processor; and
a second housing portion, which removably couples with the first housing portion, comprising:
an optical sensor comprising a plurality of source structures, a plurality of detector structures, and a first plurality of optical waveguides that optically coupled to the plurality of source structures and the plurality of detector structures; and
a second electrical connector, mating with the first electrical connector, wherein the first housing portion and second housing portion are coupled together to form a handheld oximeter such that the first and second electrical connectors mate, the handheld oximeter comprises a proximal end formed by the first housing portion and a distal end formed by the second housing portion, a joint where the first and second housing portions meet together is flush, an entirety of the joint is between the proximal and distal ends, and the first and second housing portions together are configured to be held by a hand of the user such that the thumb and index finger of the user will grip the second housing portion while the first housing portion is cradled by a webbing between the thumb and index finger of the same hand.

2. The device of claim 1 wherein the display and optical sensor are directed away from each other.

3. The device of claim 1 wherein the display is directed away from tissue being measured when the optical sensor is directed toward the tissue being measured.

4. The device of claim 1 wherein the first housing portion comprises:
a memory, housed in the first housing portion, electronically coupled to the processor;
a battery, housed in the first housing portion, coupled to and supplies power to the processor, the memory, and the display.

5. The device of claim 1 wherein the first housing portion comprises a plurality of light sources, a second plurality of waveguides optically coupled to the light sources, at least a first optical waveguide and a second optical waveguide of the second plurality of optical waveguides optically coupled to at least a first optical waveguide and a second optical waveguide of the first plurality of optical waveguides when the first and second housing portions are coupled.

6. The device of claim 5 wherein the first and second optical waveguides of the first and second pluralities of optical waveguides are optical fibers.

7. The device of claim 1 wherein the second housing portion comprises a finger rest surface, coupled to a back side surface of the second housing portion, wherein the finger rest surface is a concave surface that extends at an angle in a turn direction relative to the back side surface of the second housing portion.

8. The device of claim 1 wherein the first housing portion comprises a first rectangular tubular portion, wherein the first rectangular tubular portion comprises: a front side surface; a back side surface; a first side surface; a second side surface, wherein the front and back side surfaces are coupled together by the first and second side surfaces; and a lip on the front and back side surfaces and on the first and second side surfaces, wherein the processor is housed in the first rectangular tubular portion the first housing portion, and
the second housing portion comprises a second rectangular tubular portion, wherein the second rectangular tubular portion comprises: a front side surface; a back side surface, a first side surface; a second side surface, wherein the front and back side surfaces of the second rectangular tubing portion are coupled together by the first and second side surfaces the second rectangular tubing portion; and an edge at ends of the front and back side surfaces of the second rectangular tubular portion and at ends of the first and second side surfaces of the second rectangular tubular portion, wherein the optical sensor is at least partially housed in the second rectangular tubular portion of the second housing portion, and the joint is formed where the lip and edge of the first and second rectangular tubular portions of the first and second housing portions meet together, the joint is flush and extends around the first and second rectangular portions.

9. A method comprising:
providing a handheld oximeter housing;
providing a processor housed in the handheld oximeter housing;
providing a memory, housed in the handheld oximeter housing, electronically coupled to the processor;
providing a display, accessible from an exterior of the handheld oximeter housing, electronically coupled to the processor;
providing a first connector having a first plurality of electrical connectors that are electrically coupled to the processor;
providing a first probe tip;

providing a first plurality of light sources optically coupled to a first plurality of source structures, wherein the source structures are on a face of the first probe tip and have a first source structure arrangement;
providing a first plurality of photodetectors optically coupled to a first plurality of detector structures, wherein the first plurality of detector structures are on the face of the first probe tip and the first plurality of detector structures have a first detector structure arrangement;
providing a second connector of the first probe tip having a second plurality of electrical connectors that are electrically coupled to the first plurality of light structures and the first plurality of detector structures;
providing for removably coupling of the first probe tip to the handheld oximeter housing via coupling of the first connector to the second connector to form a handheld oximeter, which comprises a proximal end formed by the handheld oximeter housing and a distal end formed by the first probe tip;
providing a joint where the handheld oximeter housing and the first probe tip couple, wherein an entirety of the joint is between the proximal and distal ends; and
providing for the first and second plurality of electrical connectors to electrically couple when the first probe tip is removably coupled to the handheld oximeter housing.

10. The method of claim 9 comprising providing for the processor to send a control signal to the first plurality of source structures via the first and second plurality of electrical connectors when the first probe tip is removably coupled to the handheld oximeter housing and the first and second plurality of electrical connectors are electrically coupled.

11. The method of claim 10 comprising providing the processor to receive detector signals from the first plurality of detector structures via the first and second plurality of electrical connectors when the first probe tip is removably coupled to the handheld oximeter housing and the first and second electrical connectors are electrically coupled.

12. The method of claim 9 comprising:
providing a second probe tip;
providing a second plurality of source structures on a second face of the second probe tip, wherein the second plurality of source structures has a second source structure arrangement;
providing a second plurality of detector structures on the second face of the second probe tip, wherein the second plurality of detector structures has a second detector structure arrangement;
providing a third connector of the second probe tip, wherein the third connector has a third plurality of electrical connectors that are electrically coupled to the second plurality of source structures and the second plurality of detector structures;
providing for the second probe tip to replace the first probe tip on the handheld oximeter housing; and
providing for the first and third plurality of electrical connectors to be electrically coupled when the second probe tip replaces the first probe tip on the handheld oximeter housing.

13. The method of claim 12 comprising providing for the first and second detector structure arrangements to be different arrangements.

14. The method of claim 12 comprising providing for the first and second detector structure arrangements to be the same arrangements.

15. The method of claim 9 comprising:
providing a tray housing a plurality of probe tips; and
providing for one of the probe tips of the plurality of probe tips to replace the first probe tip on the handheld tissue oximeter housing.

16. The method of claim 9 comprising:
providing a latch on the first connector; and
providing for latching of the second connector of the first probe tip to the first connector via the latch on the first connector.

17. The method of claim 9 wherein the first probe tip comprises a finger rest surface, coupled to the back side surface of the first probe tip, wherein the finger rest surface is a concave surface that extends at an angle in a turn direction relative to the back side surface of the first probe tip.

18. The method of claim 9 comprising providing for the handheld oximetry housing to comprise a body portion that comprises a first rectangular tubular portion, wherein the first rectangular tubular portion comprises: a front side surface; a back side surface; a first side surface; a second side surface, wherein the front and back side surfaces are coupled together by the first and second side surfaces; and a lip on the front and back surfaces and on the first and second side surfaces, and wherein the processor and the memory are housing in the first rectangular tubular portion;
providing for the first probe tip to comprise a second rectangular tubular portion, wherein the second rectangular tubular portion comprises: a front side surface; a back side surface; a first side surface, a second side surface, wherein the front and back surfaces of the second rectangular tubular portion are coupled together by the first and second side surfaces of the second rectangular tubular portion; and an edge at ends of the front and back side surfaces of the second rectangular tubular portion and at the first and second side surfaces of the second rectangular tubular portion; and
providing for the joint to be where the lip and edge meet together when the first and second rectangular tubular portions meet together, wherein the joint is flush and extends around the first and second rectangular portions.

19. A method comprising:
providing a handheld oximeter housing;
providing a processor housed in the handheld oximeter housing;
providing a memory, housed in the handheld oximeter housing, electronically coupled to the processor;
providing a display, accessible from an exterior of the handheld oximeter housing, electronically coupled to the processor;
providing a first connector having a first plurality of electrical connectors that are electrically coupled to the processor;
providing a first probe tip;
providing a first plurality of light sources optically coupled to a first plurality of source structures, wherein the source structures are on a face of the first probe tip and have a first source structure arrangement;
providing a first plurality of photodetectors optically coupled to a first plurality of detector structures, wherein the first plurality of detector structures are on the face of the first probe tip and the first plurality of detector structures have a first detector structure arrangement;
providing a second connector of the first probe tip having a second plurality of electrical connectors that are electrically coupled to the first plurality of light sources and the first plurality of photodetectors;

providing for removably coupling the first probe tip to the handheld oximeter housing via coupling the first connector to the second connector to form a handheld oximeter, which comprises a proximal end formed by the handheld oximeter housing and a distal end formed by the first probe tip;

providing a first joint where the handheld oximeter housing and the first probe tip couple, wherein the first joint does not extend to the distal end of the handheld oximeter; and providing for the first and second electrical connectors to electrically couple when the first probe tip is removably coupled to the handheld oximeter housing;

providing a second probe tip;

providing a second plurality of light sources optically coupled to a second plurality of source structures, wherein the source structures are on a face of the second probe tip and have a second source structure arrangement;

providing a second plurality of photodetectors optically coupled to a second plurality of detector structures, wherein the second plurality of detector structures are on the face of the second probe tip and the second plurality of detector structures have a second detector structure arrangement;

providing a third connector of the second probe tip having a third plurality of electrical connectors that are electrically coupled to the second plurality of light structures and the second plurality of detector structures;

providing for removing the first probe tip from the handheld oximeter housing;

providing for removably coupling the second probe tip to the handheld oximeter housing via coupling the first connector to the third connector to form the handheld oximeter, which comprises the proximal end and the distal end formed by the second probe tip;

providing a second joint where the handheld oximeter housing and second first probe tip couple, wherein the second joint does not extend to the distal end of the handheld oximeter; and providing for the first and third electrical connectors to electrically couple when the second probe tip is removably coupled to the handheld oximeter housing.

20. The method of claim 19 wherein the first and second arrangements of the first and second pluralities of the detectors structures are the same arrangement.

21. The method of claim 19 wherein the first and second arrangements of the first and second pluralities of the detectors structures are different arrangements.

22. The method of claim 19 comprising:

providing a probe tip tray housing a plurality of probe tips including the first and the second probe tips; and removing the first probe tip from the probe tip tray after coupling the first probe tip to the handheld oximeter housing.

23. The method of claim 19 wherein the first probe tip comprises a first finger rest surface on a first back side surface of the first probe tip, wherein the first finger rest surface is a concave surface that extends at an angle in a turn direction relative to the first back side surface.

* * * * *

UNITED STATES PATENT AND TRADEMARK OFFICE
CERTIFICATE OF CORRECTION

PATENT NO. : 10,722,158 B2
APPLICATION NO. : 15/493132
DATED : July 28, 2020
INVENTOR(S) : Joseph Heanue, Scott Coleridge and Sophia Elizabeth Berger It is certified that error appears in the above-identified patent and that said Letters Patent is hereby corrected as shown below:

In the Claims

In Column 13, Lines 30-31, Claim 19, replace "structures" with --sources-- and "detector structures" with --photodetectors--.

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*